US011613508B2

(12) United States Patent
Anderson et al.

(10) Patent No.: US 11,613,508 B2
(45) Date of Patent: *Mar. 28, 2023

(54) SUBSTITUTED CATECHOL ADDITIVES IN COATINGS AND METHODS FOR USE

(71) Applicant: RHODIA OPERATIONS, Paris (FR)

(72) Inventors: Eugene J. Anderson, Marlton, NJ (US); Nemesio Martinez-Castro, Paris (FR); Lichang Zhou, Lawrenceville, NJ (US)

(73) Assignee: RHODIA OPERATIONS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,584

(22) Filed: Aug. 30, 2019

(65) Prior Publication Data

US 2020/0071252 A1  Mar. 5, 2020

Related U.S. Application Data

(60) Provisional application No. 62/724,858, filed on Aug. 30, 2018.

(51) Int. Cl.
| | |
|---|---|
| C07C 43/20 | (2006.01) |
| C09D 133/08 | (2006.01) |
| C09D 5/02 | (2006.01) |
| C09D 7/63 | (2018.01) |
| C09D 7/65 | (2018.01) |
| C07C 43/21 | (2006.01) |
| C08L 71/12 | (2006.01) |
| C07C 43/205 | (2006.01) |

(52) U.S. Cl.
CPC .......... *C07C 43/2055* (2013.01); *C07C 43/21* (2013.01); *C09D 5/024* (2013.01); *C09D 7/63* (2018.01); *C09D 7/65* (2018.01); *C09D 133/08* (2013.01); *C08L 71/12* (2013.01)

(58) Field of Classification Search
CPC ... C07C 43/2055; C07C 43/21; C09D 133/08; C09D 5/024; C09D 7/63; C09D 7/65; C08L 71/12
USPC ....................................................... 524/561
See application file for complete search history.

(56) References Cited

U.S. PATENT DOCUMENTS

| | | | |
|---|---|---|---|
| 5,770,760 A | 6/1998 | Robinson | |
| 8,673,275 B2 | 3/2014 | Kim et al. | |
| 8,993,658 B2 * | 3/2015 | Graf | B05D 3/0254 524/80 |
| 9,228,041 B2 | 1/2016 | Martinez-Castro et al. | |
| 9,309,376 B2 * | 4/2016 | Palmer, Jr. | C07C 43/164 |
| 10,029,967 B2 * | 7/2018 | Anderson, Jr. | C07C 69/54 |
| 2013/0280434 A1 * | 10/2013 | Graf | B05D 3/0254 516/77 |
| 2013/0289434 A1 * | 10/2013 | Chou | A61B 5/316 600/546 |
| 2014/0099276 A1 | 4/2014 | Yang et al. | |
| 2014/0114006 A1 | 4/2014 | Palmer, Jr. | |
| 2014/0178325 A1 | 6/2014 | Martinez-Castro et al. | |
| 2014/0256862 A1 * | 9/2014 | Palmer, Jr. | C08G 65/02 524/148 |
| 2015/0094240 A1 * | 4/2015 | Kilaas | C07C 69/40 562/42 |
| 2015/0133604 A1 | 5/2015 | Zong et al. | |
| 2015/0266804 A1 * | 9/2015 | Anderson, Jr. | C07C 41/03 524/556 |
| 2015/0266980 A1 | 9/2015 | Martinez-Castro et al. | |
| 2016/0222243 A1 | 8/2016 | Palmer, Jr. et al. | |
| 2016/0333213 A1 | 11/2016 | Zhou et al. | |
| 2018/0208782 A1 | 7/2018 | Steinmetz et al. | |
| 2020/0071441 A1 * | 3/2020 | Anderson | C09D 5/02 |
| 2020/0071442 A1 * | 3/2020 | Anderson | C09D 5/027 |

FOREIGN PATENT DOCUMENTS

JP   H01299804 A   12/1989

OTHER PUBLICATIONS

G. Pohlein, Emulsion Polymerization, Encyclopedia of Polymer Science and Engineering, vol. 6, pp. 1-51 (John Wiley & Sons, Inc., NY, NY, 1986.
A.S. Sarac, "Redox polymerization", Progress in Polymer Science 24 (1999), pp. 1149-1204.
Extended European Search Report dated Sep. 1, 2022, for EP 19856351.2 filed Aug. 30, 2019, 10 pages.
Supplementary European Search Report dated Apr. 21, 2022, for EP 19853435 filed Aug. 30, 2019, 4 pages.
International Search Report dated Dec. 24, 2019, for PCT/US2019/048998 filed Aug. 30, 2019.
European Patent Office Communication dated Sep. 1, 2022, for EP Patent application No. 19856351 filed Aug. 30, 2019.

* cited by examiner

*Primary Examiner* — Michael M. Bernshteyn
(74) *Attorney, Agent, or Firm* — Vorys, Safer, Seymour and Pease LLP; Anthony P. Venturino; Maryellen Feehery Hank

(57) ABSTRACT

Disclosed are novel catechol dditives and the like, methods of preparing, as well as compositions and methods using such compositions in various applications. Also provided is a method of preparing an aqueous coating composition such as a latex paint including the above components.

21 Claims, No Drawings

SUBSTITUTED CATECHOL ADDITIVES IN COATINGS AND METHODS FOR USE

CROSS-REFERENCE TO RELATED APPLICATIONS

This application claims the benefit of U.S. Provisional Application No. 62/724,858 filed Aug. 30, 2018, incorporated herein by reference in its entirety.

FIELD OF THE INVENTION

The present invention relates to novel catechol surfactants, additives, emulsifiers, and the like, methods of preparing, as well as compositions and methods using such compositions in various applications.

BACKGROUND OF THE INVENTION

Dispersant additives assist to disperse small or fine particles into a liquid medium. Such dispersants are useful in coatings, plastics, cosmetics, and the like. Suitable dispersants are able to disperse, as finely and efficiently as possible, such fine or small particles into a liquid medium, which remains stable over a certain time. One problem with currently available dispersants, however, is that the dispersion of fine particles in liquids is unstable in that the particles tend to agglomerate or flocculate causing changes in properties, e.g., varying shades of color, unequal pigmentation, changes in rheology, as well as other undesirable properties, over time in the product where disperability is desired.

In particular, coatings can have a wide variety of miscellaneous additives, which are usually added in small amounts, yet provide a significant effect on the product. Some examples include additives to modify surface tension, improve flow properties, improve the finished appearance, increase wet edge, improve pigment stability, impart antifreeze properties, control foaming, control skinning, etc. Other types of additives include catalysts, thickeners, stabilizers, emulsifiers, texturizers, adhesion promoters, UV stabilizers, flatteners (de-glossing agents), biocides to fight bacterial growth, and the like. Additives normally do not significantly alter the percentages of individual components in a formulation In the paints and coatings additives market, surfactants are used as wetting, anti-foaming and dispersing agents.

SUMMARY OF THE INVENTION

Additives or thickeners may be used in a variety of liquid systems including aqueous systems such as paints, aqueous inks, and personal care products and compositions for treating subterranean formations. The additives improve the rheological properties by also affecting the dispersion, suspension and emulsification of pigments, binders and other solids within a vehicle.

The present invention relates to the use of a particular family of alkoxylated compounds with bulky hydrophobic groups, e.g., alkoxylated substituted catechols, for improving properties in a composition such as, in paints and coatings, dispersability, freeze-thaw stability, open time, low temperature film formation, stain resistance, film gloss, hiding and scrub resistance, foam resistance, block resistance, adhesion and water sensitivity, among others.

In one aspect, described herein are additives, emulsifiers, dispersants and/or surfactants according to structure (D.I):

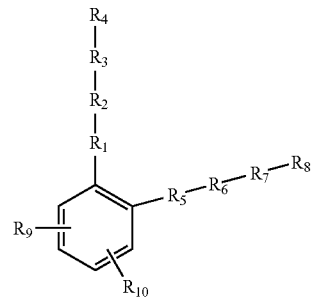

(D.I)

wherein $R_1$ and $R_5$ are independently absent or a bivalent linking group, $R_2$ and $R_6$ are independently a bivalent polyether group, $R_3$ and $R_7$ are independently absent or a bivalent linking group, and $R_4$ and $R_8$ are independently an anionic group, a cationic group or a nonionic group; and wherein $R_9$ and $R_{10}$ are independently selected from the following structures D.Ia, D.Ib, D.Ic, D.Id:

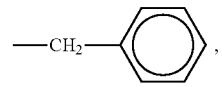

D.Ia

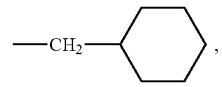

D.Ib

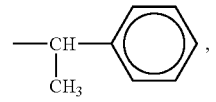

D.Ic

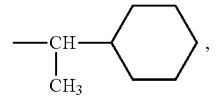

D.Id or a $C_2$-$C_{30}$ branched or linear alkyl group or alkenyl group.

In one embodiment, $R_4$ and $R_8$ are independently selected from —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a counterion. In another embodiment, $R_2$ and $R_6$ are independently selected from —[CH($R_{20}$)CH($R_{21}$)O]$_x$—, wherein x is an integer of from 0 to 100, and $R_{20}$ and $R_{21}$ are independently selected from any of the following:

H; —CH$_2$OH; phenyl; —CH$_2$Cl;

a $C_1$-$C_{30}$ straight or branched alkyl or alkenyl;

—CH$_2$OR$_{22}$ wherein $R_{22}$ is $C_1$-$C_{30}$ straight or branched alkyl or alkenyl, phenyl, or alkyl substituted phenyl; or R'COOCH$_2$— where R' is $C_1$-$C_{30}$ straight or branched alkyl or alkenyl.

In another aspect, described herein are low VOC latex coating compositions comprising:

(a) at least one latex polymer;
(b) optionally, at least one pigment;
(c) water; and
(d) an additive present in an amount effective to impart freeze-thaw stability, having structure (D.I):

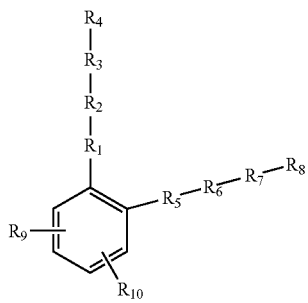

(D.I)

wherein
$R_1$ and $R_5$ are independently absent or a bivalent linking group,
$R_2$ and $R_6$ are independently a bivalent polyether group,
$R_3$ and $R_7$ are independently absent or a bivalent linking group, and
$R_4$ and $R_8$ are independently an anionic group, a cationic group or a nonionic group; and
wherein $R_9$ and $R_{10}$ are independently selected from the following structures D.Ia, D.Ib, D.Ic, D.Id:

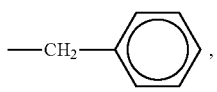

D.Ia

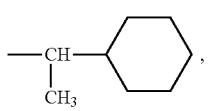

D.Ib

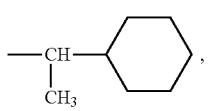

D.Ic

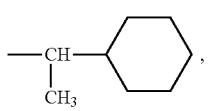

D.Id

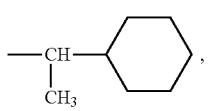

or a $C_2$-$C_{30}$ branched or linear alkyl group or alkenyl group.

In yet another aspect, described herein are methods for imparting freeze-thaw stability on a low VOC coating composition comprising adding to the composition an effective amount of an additive according to structural to structure (D.I):

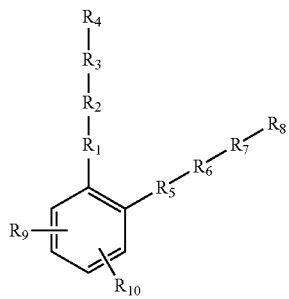

(D.I)

wherein
$R_1$ and $R_5$ are independently absent or a bivalent linking group,
$R_2$ and $R_6$ are independently a bivalent polyether group,
$R_3$ and $R_7$ are independently absent or a bivalent linking group, and
$R_4$ and $R_8$ are independently an anionic group, a cationic group or a nonionic group; and
wherein $R_9$ and $R_{10}$ are independently selected from the following structures D.Ia, D.Ib, D.Ic, D.Id:

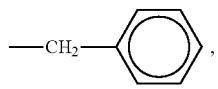

D.Ia

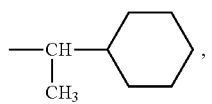

D.Ib

D.Ic

D.Id or a $C_2$-$C_{30}$ branched or linear alkyl group or alkenyl group; wherein the low VOC comprises at least one latex polymer, water and, optionally, at least one pigment.

In one embodiment, M+ is a cation including but not limited to $H^+$, $Na^+$, $NH_4^+$, $K^+$ or $Li^+$. In one embodiment, $R_4$ and $R_8$ are each independently alkyl, hydroxyalkyl, alkoxyalkyl, cycloalkyl, aryl, arylalkyl, or aryloxy. In another embodiment, $R_4$ and $R_8$ are each independently ($C_1$-$C_{22}$) alkyl, ($C_1$-$C_{22}$)hydroxyalkyl, ($C_2$-$C_{22}$)alkoxyalkyl, ($C_6$-$C_{24}$) cycloalkyl, ($C_6$-$C_{40}$)aryl, or ($C_7$-$C_{40}$)arylalkyl, more typically ($C_2$-$C_{12}$)alkyl In one embodiment, $R_4$ and $R_8$ are each independently an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

The invention is also directed to a homogeneous, pourable liquid which improves properties in aqueous coatings, for example, improved water sensitivity. These improved properties are due to a reduction in the use level of the thickeners as described herein, needed to achieve a desired rheological profile.

The aqueous coating compositions of the invention typically include at least one latex polymer derived from at least one monomer, for example acrylic monomers. The at least one latex polymer in the aqueous coating composition can be a pure acrylic, a styrene acrylic, a vinyl acrylic or an acrylated ethylene vinyl acetate copolymer and is more preferably a pure acrylic. The at least one latex polymer is preferably derived from at least one acrylic monomer selected from the group consisting of acrylic acid, acrylic acid esters, methacrylic acid, and methacrylic acid esters. For example, the at least one latex polymer can be a butyl acrylate/methyl methacrylate copolymer or a 2-ethylhexyl acrylate/methyl methacrylate copolymer. Typically, the at least one latex polymer is further derived from one or more monomers selected from the group consisting of styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, and $C_4$-$C_8$ conjugated dienes.

Latex paint formulations typically comprise additives, e.g., at least one pigment. In a preferred embodiment of the invention the latex paint formulation includes at least one pigment selected from the group consisting of $TiO_2$, $CaCO_3$, clay, aluminum oxide, silicon dioxide, magnesium oxide, sodium oxide, potassium oxide, talc, barytes, zinc oxide, zinc sulfite and mixtures thereof. More preferably the at least one pigment includes TiO2, calcium carbonate or clay.

In addition to the above components, the aqueous coating composition can include one or more additives selected from the group consisting of dispersants, surfactants, rheology modifiers, defoamers, thickeners, biocides, mildewcides, colorants, waxes, perfumes and co-solvents.

Compositions of the present invention may have an absence of one or more of anionic surfactant, cationic surfactant, nonionic surfactant, zwitterionic surfactant, and/or amphoteric surfactant.

These and other features and advantages of the present invention will become more readily apparent to those skilled in the art upon consideration of the following detailed description, which describe both the preferred and alternative embodiments of the present invention.

DETAILED DESCRIPTION OF THE PREFERRED EMBODIMENTS

The present invention relates to, in one embodiment, the use of a particular family of copolymers for latex dispersions, binders, paints and coatings. Described herein are aqueous compositions, for example, aqueous coating compositions. The aqueous compositions of the invention are aqueous polymer dispersions which include at least one latex polymer. Paints or other aqueous coatings of the present invention typically further include at least one pigment. In one embodiment, the latex has a Tg of less than 10° C., more typically less than 5° C., still more typically in the range from 5 to −10° C., e.g., 0° C.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tetracontyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "arylalkyl" means an alkyl group substituted with one or more aryl groups, more typically a ($C_1$-$C_{18}$)alkyl substituted with one or more ($C_6$-$C_{14}$)aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$) alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a $(C_1-C_{22})$alkyl radical, that is substituted with one or more hydroxyl groups, such as for example, hydroxymethyl, hydroxyethyl, hydroxypropyl, and hydroxydecyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl (meth)acrylate" means butyl acrylate and/or butyl methacrylate.

As used herein, "molecular weight" in reference to a polymer or any portion thereof, means to the weight-average molecular weight ("$M_w$") of the polymer or portion. $M_w$ of a polymer is a value measured by gel permeation chromatography (GPC) with an aqueous eluent or an organic eluent (for example dimethylacetamide, dimethylformamide, and the like), depending on the composition of the polymer, light scattering (DLS or alternatively MALLS), viscometry, or a number of other standard techniques. $M_w$ of a portion of a polymer is a value calculated according to known techniques from the amounts of monomers, polymers, initiators and/or transfer agents used to make the portion.

As used herein, the indication that a radical may be "optionally substituted" or "optionally further substituted" means, in general, unless further limited either explicitly or by the context of such reference, such radical may be substituted with one or more inorganic or organic substituent groups, for example, alkyl, alkenyl, aryl, arylalkyl, alkaryl, a hetero atom, or heterocyclyl, or with one or more functional groups capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

As used herein, the term "surfactant" means a compound that reduces surface tension when dissolved in water.

"Surfactant effective amount" means the amount of the surfactant that provides a surfactant effect to enhance the stability of emulsions of the polymers.

I. Additive

In one embodiment, the compound of the present invention is a surfactant or characterized as a surfactant. In one embodiment, the compound of the present invention is an emulsifier or characterized as an emulsifier. In one embodiment, the compound of the present invention is a dispersant or characterized as a dispersant. In one embodiment, the compound of the present invention is an additive or characterized as an additive. In yet another embodiment, the compound of the present invention is characterized as at least one of an emulsifier, dispersant, surfactant or additive.

In one embodiment, the compound of the present invention is according to structure (D.I):

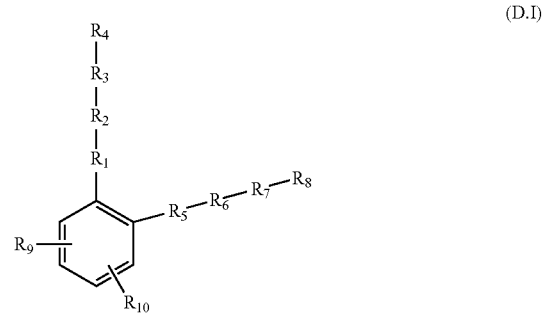

(D.I)

wherein
$R_1$ and $R_5$ are independently absent or a bivalent linking group,
$R_2$ and $R_6$ are independently a bivalent polyether group,
$R_3$ and $R_7$ are independently absent or a bivalent linking group, and
$R_4$ and $R_8$ are independently an anionic group, a cationic group or a nonionic group; and
wherein $R_9$ and $R_{10}$ are independently selected from the following structures D.Ia, D.Ib, D.Ic, D.Id:

D.Ia

D.Ib

D.Ic

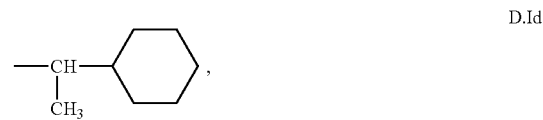

D.Id or a $C_2-C_{30}$ branched or linear alkyl group or alkenyl group.

The $C_2-C_{30}$ branched or linear alkyl group or alkenyl group can be a $C_3-C_{14}$ branched or linear alkyl group or alkenyl group, or a $C_5-C_{14}$ branched or linear alkyl group or alkenyl group, or a $C_6-C_{14}$ branched or linear alkyl group or alkenyl group, or a $C_8-C_{12}$ branched or linear alkyl group or alkenyl group, or a $C_4-C_{12}$ branched or linear alkyl group or alkenyl group.

Preferably, The $C_2-C_{30}$ branched or linear alkyl group or alkenyl group can be a $C_8-C_{12}$ branched or linear alkyl group or alkenyl group, or a $C_6$-$C_{12}$ branched or linear alkyl group or alkenyl group, or a $C_4$-$C_{12}$ branched or linear alkyl group or alkenyl group.

In one embodiment, the $C_2$-$C_{30}$ branched or linear alkyl group or alkenyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In one embodiment, $R_4$ and $R_8$ are independently selected from —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, $R_4$ and $R_8$ are independently selected from alkyl, hydroxyalkyl, alkoxyalkyl, cycloalkyl, aryl, arylalkyl, or aryloxy. In another embodiment, $R^{18}$ is ($C_1$-$C_{22}$) alkyl, ($C_1$-$C_{22}$)hydroxyalkyl, ($C_2$-$C_{22}$)alkoxyalkyl, ($C_6$-$C_{24}$) cycloalkyl, ($C_6$-$C_{40}$)aryl, or ($C_7$-$C_{40}$)arylalkyl, more typically ($C_2$-$C_{12}$)alkyl In one embodiment, $R_4$ and $R_8$ are independently selected from an inorganic or organic substituent group, such as, for example, alkyl, alkenyl, aryl, aralkyl, alkaryl, a hetero atom, or heterocyclyl, or with one or more functional groups such as hydroxyl, carbonyl, carboxyl, amino, imino, amido, phosphonic acid, sulphonic acid, or inorganic and organic esters thereof, such as, for example, sulphate or phosphate, or salts thereof.

In one embodiment, $R_1$, $R_3$, $R_5$, $R_7$ are each independently O, a bivalent hydrocarbon group, even more typically a methylene group or chain of from 2 to 6 methylene units, or a bivalent alkyleneoxyl group, such as ethyleneoxy. In one embodiment, $R_1$, $R_3$, $R_5$, $R_7$ are independently according to structure (D.VIII):

—(CH$_2$)$_b$-A-         (D.IX)

wherein A is O or absent, and b is an integer of from 1 to 6.

In some embodiments, $R_2$ and $R_6$ are independently a bivalent polyether group comprising a linear chain of from 2 to 100 units, each of which may independently be ($C_2$-$C_4$)oxyalkylene, more typically, ($C_2$-$C_3$)oxyalkylene. In one embodiment, $R_2$ and $R_6$ are independently a bivalent polyether group comprising a chain of from 2 to 100 polymerized oxyethylene units and oxypropylene units, which may be arranged alternately, randomly, or in blocks. In one embodiment, $R_2$ and $R_6$ are independently a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R_1$, $R_3$, $R_5$, $R_7$ are each independently —(CH$_2$)$_x$O—, wherein x is an integer from 1 to 20 (e.g., use of styrenated benzyl alcohols)

In another embodiment, $R_1$, $R_3$, $R_5$, $R_7$ are each independently —CH$_2$CH(OH)CH$_2$O— or —CH$_2$CH(CH$_2$OH)O— (e.g., use of epichlorohydrin as coupling agent)

In one embodiment, $R_2$ and $R_6$ are independently:
—[CH(R$_{20}$)CH(R$_{21}$)O]$_x$— wherein x is an integer of from 0 to 100, and R$_{20}$ and R$_{21}$ are independently selected from any of the following:
H; —CH$_2$OH; phenyl; —CH$_2$Cl;
a $C_1$-$C_{30}$ straight or branched alkyl or alkenyl;
—CH$_2$OR$_{22}$ wherein R$_{22}$ is $C_1$-$C_{30}$ straight or branched alkyl or alkenyl, phenyl, or alkyl substituted phenyl; or
R'COOCH$_2$— where R' is $C_1$-$C_{30}$ straight or branched alkyl or alkenyl.

Applications

When surface active alkoxylated tri-substituted aromatic compound is employed as an emulsifier in emulsion polymerization to form the latex polymer, the latex polymer is made from a mixture wherein the surface active emulsifier utilized is. In one embodiment, the emulsifier is added in an amount greater than 1% by weight of the polymer or monomers used to form the latex polymer. In one embodiment, the emulsifier is added in an amount greater than 1.3% by weight of the polymer or monomers used to form the latex polymer, in an amount greater than 1.6% by weight of the polymer or monomers used to form the latex polymer, typically in an amount greater than about 2% by weight of the polymer or monomers used to form the latex polymer, more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains an emulsifier in an amount greater than about 8% by weight of the polymer or monomers used to form the latex polymer, or greater than about 10% by weight of the polymer or monomers. In another embodiment, the emulsifier is added is between about 1.6% and 7.5% by weight of the polymer or monomers used to form the latex polymer. In another embodiment, emulsifier added is between about 1.6% and 45% by weight of the polymer or monomers used to form the latex polymer, typically between about 1.6% and 35% by weight of the polymer or monomers used to form the latex polymer In another embodiment the compounds as described herein can be used as an additive to an already formed aqueous dispersion of latex polymer.

In some embodiments, the additive is a freeze-thaw additive that can be added any point in the production of the aqueous coating composition, including but not limited to during the emulsification step, during formulation, etc. It is also understood that the freeze-thaw additive can be post-added to the aqueous coating composition or a concentrate thereof.

This results in an aqueous composition comprising the surface active alkoxylated compound and the latex polymer. When the surface active alkoxylated compound is employed as an additive to an already formed aqueous latex dispersion, the resulting composition has alkoxylated compound additive in an amount of about 1 to 10, Typically 2 to 8 or 2 to 6, parts per 100 parts by weight of monomers used to form the latex polymer.

In another embodiment the above-described surface active compound of any of the structural formulas above can be used as an additive to an during formulation of paint or aqueous coating composition. Formulation is the stage at which additives are added to a base aqueous latex polymer dispersion to make it into final product such as a paint or coating. When the surface active alkoxylated compound is employed as an additive to an already formed paint or aqueous coating composition, e.g., aqueous latex coating dispersion, the resulting composition has alkoxylated compound additive typically in an amount greater than about 1.3% by weight of the polymer or monomers used to form the latex polymer, more typically in an amount greater than about 1.6% by weight of the polymer or monomers used to form the latex polymer, yet more typically in an amount greater than about 2% by weight of the polymer or monomers used to form the latex polymer, even more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains surface active alkoxylated compound in an amount between about 1.6% and 7.5% by weight of the polymer or monomers used to form the latex polymer. In another embodiment, the latex coating composition contains surface active alkoxylated compound in an amount between about 1.6% and 45% by weight of the polymer or monomers used to form the latex polymer, typically between about 1.6% and 35%. Pigment is a typical additive, for example, added during formulation of paint from raw aqueous latex polymer dispersion.

The aqueous coating compositions of the present invention are freeze-thaw stable where the freeze-thaw additive is present in the aqueous coating composition in the amounts by weight of the polymer as described above, where the polymer can have a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm. As described above, the mean particle size is typically between about 75 nm to about 400 nm. The aqueous coating composition can be characterized by an open time of greater than about 2 minutes, an open time of greater than about 4 minutes, an open time of greater than about 6 minutes or an open time of greater than about 12 minutes.

The present invention further includes a method of preparing a paint or aqueous coating composition, comprising adding the at least one surface active alkoxylated compound of any of the structural formulas above during formulation of paint or aqueous coating composition comprising at least one pigment and other additives to produce the final paint or aqueous coating composition. The addition of the surface active alkoxylated compound surfactant (emulsifier) during formulation of paint or aqueous coating composition forms a coating composition having a lower VOC content while maintaining the freeze-thaw stability of the aqueous coating composition at desirable levels.

As mentioned above, the aqueous coating composition in some embodiments can include less than 2.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More typically, the aqueous coating composition includes less than 1.0% or is substantially free (e.g. includes less than 0.1%) of anti-freeze agents. Accordingly, the aqueous coating composition of the invention typically has a VOC level of less than about 100 g/L and more typically less than or equal to about 50 g/L. Despite the fact that the aqueous coating compositions of the invention include little or no anti-freeze agents, the compositions possess freeze-thaw stabilities at levels desirable in the art.

For example, the aqueous coating compositions of the invention can be subjected to freeze-thaw cycles using ASTM method D2243-82 or ASTM D2243-95 without coagulation.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more typically from about 35% to about 80% by weight water. Stated differently, the total solids content of the aqueous coating composition is typically from about 15% to about 90%, more typically, from about 20% to about 65%.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

In formulating latexes and latex paints/coatings, physical properties that may be considered include, but are not limited to, viscosity versus shear rate, ease of application to surface, spreadability, and shear thinning.

Emulsion polymerization is discussed in G. Pohlein, "Emulsion Polymerization", Encyclopedia of Polymer Science and Engineering, vol. 6, pp. 1-51 (John Wiley & Sons, Inc., New York, N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The monomers typically employed in emulsion polymerization to make latex for latex paint include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof. This is further discussed below in the section entitled "Latex Monomers".

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like. Commonly used redox initiation systems are described e.g., by A. S. Sarac in Progress in Polymer Science 24(1999), 1149-1204.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Emulsion polymerization occurs in the presence of an emulsifier. Typically the mixture contains 0.01 to 6 wt % (or in other embodiment 0.05 to 6 wt %) emulsifier based on weight of latex monomers.

Aside from the compounds as described herein, typical emulsifiers are ionic or non-ionic surfactants polymerizable or non-polymerizable in the aqueous coating composition including latex polymer. Suitable ionic and nonionic surfactants are alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The polymer latex binder can be produced by first preparing an initiator solution comprising the initiator and water. A monomer pre-emulsion is also prepared comprising one or more surfactants (emulsifiers), and other latex monomers to be used to form the latex polymer, water, and additional additives such as NaOH.

Thus, a typical process of emulsion polymerization preferably involves charging water to a reactor and feeding as separate streams a pre-emulsion of the monomer and a solution of the initiator. In particular, the polymer latex binder can be prepared using emulsion polymerization by feeding the monomers used to form the latex binder to a reactor in the presence of at least one initiator and at least one surfactant and polymerizing the monomers to produce the latex binder. Typically the initiator solution and monomer pre-emulsion are continuously added to the reactor over a predetermined period of time (e.g. 1.5-5 hours) to cause polymerization of latex monomers to produce the latex polymer.

Prior to the addition of the initiator solution and the monomer pre-emulsion, a seed latex such as a polystyrene seed latex can be added to the reactor. For example, a small amount of the pre-emulsion and a portion of the initiator may be charged initially at the reaction temperature to produce "seed" latex. The "seed" latex procedure results in better particle-size reproducibility.

Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, namely initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

The reactor is operated at desired reaction temperature at least until all the monomers are fed to produce the polymer latex binder. Once the polymer latex binder is prepared, it is preferably chemically stripped thereby decreasing its residual monomer content. Preferably, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24(1999), 1149-1204, to the latex binder at an elevated temperature and for a predetermined period of time (e.g. 0.5 hours). The pH of the latex binder can then be adjusted and other additives added after the chemical stripping step.

In the above emulsions, the polymer preferably exists as a generally spherical particle, dispersed in water, with a diameter of about 50 nanometers to about 500 nanometers.

For purposes of this description, monomers from which latex polymers may be derived are termed "latex monomers".

The latex monomers fed to a reactor to prepare the polymer latex binder preferably include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, (alpha)-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR neo vinyl esters by ExxonMobil Chemical Company), itaconic acid, crotonic acid, maleic acid, fumaric acid, and ethylene. It is also possible to include C4-C8 conjugated dienes such as 1,3-butadiene, isoprene or chloroprene. Commonly used monomers in making acrylic paints are butyl acrylate, methyl methacrylate, ethyl acrylate and the like. Preferably, the monomers include one or more monomers selected from the group consisting of n-butyl acrylate, methyl methacrylate, styrene and 2-ethylhexyl acrylate.

The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In typical acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The latex polymer dispersion preferably includes from about 30 to about 75% solids and a mean latex particle size of from about 70 to about 650 nm. The latex polymer is preferably present in the aqueous coating composition in an amount from about 5 to about 60 percent by weight, and more preferably from about 8 to about 40 percent by weight (i.e. the weight percentage of the dry latex polymer based on the total weight of the coating composition).

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

VI. Other Additives

As described above, latex paints and coatings may contain various adjuvants.

The aqueous coating compositions of the invention include less than 2% by weight and preferably less than 1.0% by weight of anti-freeze agents based on the total weight of the aqueous coating composition. For example, the aqueous coating compositions may be substantially free of anti-freeze agents.

The aqueous coating composition typically includes at least one pigment. The term "pigment" as used herein includes non-film-forming solids such as pigments, extenders, and fillers. The at least one pigment is preferably selected from the group consisting of $TiO_2$ (in both anastase and rutile forms), clay (aluminum silicate), $CaCO_3$ (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), and ATTAGELS (commercially available from Engelhard). More preferably, the at least one pigment includes $TiO_2$, $CaCO_3$ or clay. Generally, the mean particle sizes of the pigments range from about 0.01 to about 50 microns. For example, the $TiO_2$ particles used in the aqueous coating composition typically have a mean particle size of from about 0.15 to about 0.40 microns. The pigment can be added to the aqueous coating composition as a powder or in slurry form. The pigment is preferably present in the aqueous coating composition in an amount from about 5 to about 50 percent by weight, more preferably from about 10 to about 40 percent by weight.

The coating composition can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, additional biocides, additional mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more preferably from about 1 to about 10% by weight based on the total weight of the coating composition.

The aqueous coating composition typically includes less than 10.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More preferably, the aqueous coating composition includes less than 5.0% or is substantially free (e.g. includes less than 0.1%) of anti-freeze agents. Accordingly, the aqueous coating composition of the invention preferably has a VOC level of less than about 100 g/L and more preferably less than or equal to about 50 g/L.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more preferably from about 35% to about 80% by weight water. Stated differently, the total solids content of the aqueous coating composition is typically from about 15% to about 90%, more preferably, from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, additional biocides, additional mildewcides, colorants, waxes, and the like, that do not evaporate upon drying of the coating composition.

X. Home Care or Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, fabric softener, surfactants, builders, binders, bleach and fragrances.

In an embodiment the home care or industrial cleaning composition for cleaning fabrics or hard surfaces comprising, the composition of the present invention and a surfactant and a home care or industrial cleaner benefit agent.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

It should be apparent embodiments other than those expressly described above come within the spirit and scope of the present invention. Thus, the present invention is not defined by the above description but by the claims appended hereto.

What is claimed is:

1. A surface active compound according to structure (D.I):

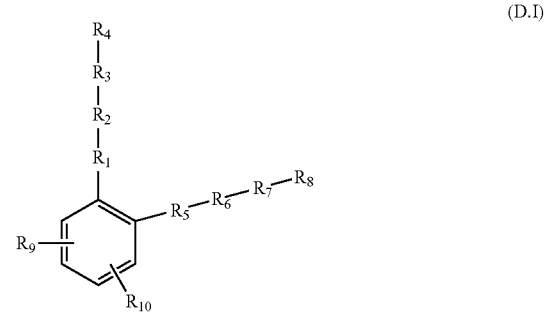

(D.I)

wherein $R_1$ and $R_5$ are independently absent or a bivalent linking group, $R_2$ and $R_6$ are independently a bivalent polyether group, $R_3$ and $R_7$ are independently absent or a bivalent linking group, and $R_4$ and $R_8$ are independently an anionic group, a cationic group or a nonionic group; and wherein $R_9$ and $R_{10}$ are independently selected from the following structures D.Ia, D.Ib, D.Ic, D.Id:

D.Ia

D.Ib

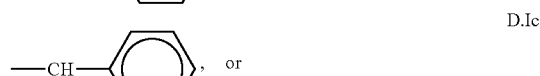

D.Ic

D.Id or a $C_2$-$C_{30}$ branched or linear alkyl group or alkenyl group.

2. The compound of claim 1, wherein $R_4$ and $R_8$ are independently selected from —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, phosphonate (—PO$_3^-$M$^+$), phosphate (PO$_4^-$M$^+$), sulfate (SO$_4^-$M$^+$), sulfonate (SO$_3^-$M$^+$), carboxylate (COO$^-$M$^+$), a nonionic group, or a quaternary ammonium ion, wherein M+ is a counterion.

3. The surface active compound of claim 1 wherein R$_2$ and R$_6$ are independently selected from —[CH(R$_{20}$)CH(R$_{21}$)O]$_x$—, wherein x is an integer of from 2 to 100, and R$_{20}$ and R$_{21}$ are independently selected from any of the following:
   H; —CH$_2$OH; phenyl; —CH$_2$Cl;
   a C$_1$-C$_{30}$ straight or branched alkyl or alkenyl;
   —CH$_2$OR$_{22}$ wherein R$_{22}$ is C$_1$-C$_{30}$ straight or branched alkyl or alkenyl, phenyl, or alkyl substituted phenyl; or
   R'COOCH$_2$— where R' is C$_1$-C$_{30}$ straight or branched alkyl or alkenyl.

4. The surface active compound of claim 1 wherein the C$_2$-C$_{30}$ branched or linear alkyl group or alkenyl group is a C$_3$-C$_{14}$ branched or linear alkyl group.

5. The surface active compound of claim 1 wherein the C$_2$-C$_{30}$ branched or linear alkyl group or alkenyl group is a C$_6$-C$_{14}$ branched or linear alkyl group.

6. The surface active compound of claim 1 wherein the C$_2$-C$_{30}$ branched or linear alkyl group or alkenyl group is a C$_8$-C$_{12}$ branched or linear alkyl group.

7. The surface active compound of claim 1 wherein the C$_2$-C$_{30}$ branched or linear alkyl group or alkenyl group is a C$_4$-C$_{12}$ branched or linear alkyl group or alkenyl group.

8. A low VOC latex coating composition comprising:
   (a) at least one latex polymer;
   (b) optionally, at least one pigment;
   (c) water; and
   (d) an additive present in an amount effective to impart freeze-thaw stability, having structure (D.I):

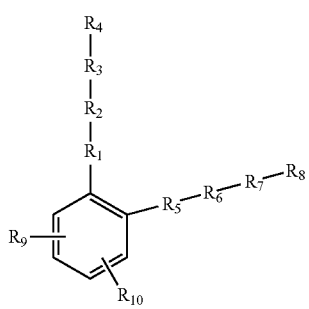

(D.I)

wherein
R$_1$ and R$_5$ are independently absent or a bivalent linking group,
R$_2$ and R$_6$ are independently a bivalent polyether group,
R$_3$ and R$_7$ are independently absent or a bivalent linking group, and
R$_4$ and R$_8$ are independently an anionic group, a cationic group or a nonionic group; and
wherein R$_9$ and R$_{10}$ are independently selected from the following structures D.Ia, D.Ib, D.Ic, D.Id:

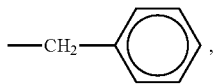

D.Ia

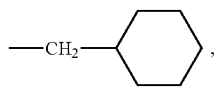

D.Ib

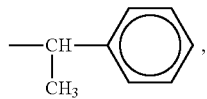

D.Ic

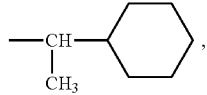

D.Id or a C$_2$-C$_{30}$ branched or linear alkyl group or alkenyl group.

9. A method for imparting freeze-thaw stability on a low VOC coating composition comprising adding to the composition an additive according to structure (D.I):

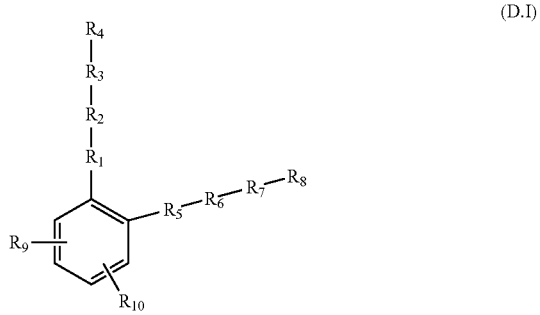

(D.I)

wherein
R$_1$ and R$_5$ are independently absent or a bivalent linking group,
R$_2$ and R$_6$ are independently a bivalent polyether group,
R$_3$ and R$_7$ are independently absent or a bivalent linking group, and
R$_4$ and R$_8$ are independently an anionic group, a cationic group or a nonionic group; and
wherein R$_9$ and R$_{10}$ are independently selected from the following structures D.Ia, D.Ib, D.Ic, D.Id:

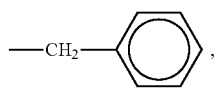

D.Ia

D.Ib

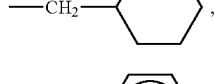

D.Ic

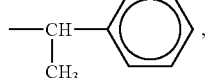

D.Id

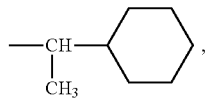

or a $C_2$-$C_{30}$ branched or linear alkyl group or alkenyl group;

wherein the low VOC comprises at least one latex polymer, water and, optionally, at least one pigment.

10. The method of claim 9 comprising greater than 0.5% of the additive by weight of the polymer.

11. The method of claim 9 comprising greater than 1.3% of the additive by weight of the polymer.

12. The method of claim 9 comprising greater than 1.6% of the additive by weight of the polymer.

13. The method of claim 9 comprising greater than 1% of the additive by weight of the polymer.

14. The composition of claim 8 comprising greater than 0.5% of the additive by weight of the polymer.

15. The composition of claim 8 comprising greater than 1.3% of the additive by weight of the polymer.

16. The composition of claim 8 comprising greater than 1.6% of the additive by weight of the polymer.

17. The composition of claim 8 comprising greater than 1% of the additive by weight of the polymer.

18. The surface active compound of claim 1 wherein the $R_4$ and $R_8$ are independently an anionic group.

19. The surface active compound of claim 1 wherein the $R_4$ and $R_8$ are independently a cationic group.

20. The surface active compound of claim 1 wherein the $R_4$ and $R_8$ are independently a nonionic group.

21. The surface active compound of claim 1,
wherein $R_4$ and $R_8$ are independently selected from
—OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, phosphonate (—PO$_3^-$M$^+$), phosphate (PO$_4^-$M$^+$), sulfate (SO$_4^-$M$^+$), sulfonate (SO$_3^-$M$^+$), carboxylate (COO$^-$M$^+$), a nonionic group, or a quaternary ammonium ion, wherein M+ is a counterion, alkyl, hydroxyalkyl, alkoxyalkyl, cycloalkyl, aryl, arylalkyl, or aryloxy, alkenyl, aralkyl, alkaryl, a hetero atom, or heterocyclyl, or with one or more functional groups selected from hydroxyl, carbonyl, carboxyl, amino, imino, amido, phosphonic acid, sulphonic acid, or inorganic and organic esters thereof;

wherein $R_2$ and $R_6$ are independently selected from a bivalent polyether group comprising a linear chain of from 2 to 100 units, each of which may independently be ($C_2$—$C_4$)oxyalkylene, —[CH(R$_{20}$)CH(R$_{21}$)O]$_x$-, wherein x is an integer of from 2 to 100, and $R_{20}$ and $R_{21}$ are independently selected from any of the following:

H; —CH$_2$OH; phenyl; —CH$_2$Cl;

a $C_1$-$C_{30}$ straight or branched alkyl or alkenyl;

-CH$_2$OR$_{22}$ wherein $R_{22}$ is $C_1$-$C_{30}$ straight or branched alkyl or alkenyl, phenyl, or alkyl substituted phenyl; or R'COOCH$_2$—where R' is $C_1$-$C_{30}$ straight or branched alkyl or alkenyl, wherein $R_1$, $R_3$, $R_5$, $R_7$ are independently the bivalent linking group selected from —(CH$_2$)$_x$O—, wherein x is an integer from 1 to 20, —CH$_2$CH(OH)CH$_2$O— or —CH$_2$CH(CH$_2$OH)O—.

* * * * *